US 6,530,950 B1

(12) United States Patent
Alvarado et al.

(10) Patent No.: US 6,530,950 B1
(45) Date of Patent: Mar. 11, 2003

(54) INTRALUMINAL STENT HAVING COAXIAL POLYMER MEMBER

(75) Inventors: Angelica Alvarado, Santa Clara, CA (US); Robert Eury, Cupertino, CA (US); Irina D. Pomerantseva, Mountain View, CA (US); Michael Froix, Mountain View, CA (US)

(73) Assignee: Quanam Medical Corporation, Santa Clara, CA (US)

( * ) Notice: Subject to any disclaimer, the term of this patent is extended or adjusted under 35 U.S.C. 154(b) by 0 days.

(21) Appl. No.: 09/632,482

(22) Filed: Aug. 3, 2000

Related U.S. Application Data

(62) Division of application No. 09/335,438, filed on Jun. 17, 1999, now abandoned.
(60) Provisional application No. 60/115,609, filed on Jan. 12, 1999.

(51) Int. Cl.$^7$ .............................. A61F 2/06; C08F 118/02
(52) U.S. Cl. .......................... 623/1.13; 623/1; 623/1.2; 623/1.16; 623/12; 623/1.42; 623/1.46; 526/319; 526/320; 526/323.1; 526/329; 526/329.2; 526/329.5

(58) Field of Search ........................ 623/1, 1.13, 1.28, 623/12, 1.16, 1.2, 1.42, 1.1, 1.46; 526/319, 320, 323.1, 329, 329.2, 329.5

(56) References Cited

U.S. PATENT DOCUMENTS

| 5,163,952 A | * | 11/1992 | Froix ........................... 623/1 |
| 5,383,928 A | * | 1/1995 | Scott et al. .................... 623/1 |
| 5,603,722 A | * | 2/1997 | Phan et al. ................. 606/198 |
| 5,607,467 A | * | 3/1997 | Froix ........................... 623/1 |
| 5,637,113 A | * | 6/1997 | Tartaglia et al. ............... 623/1 |
| 5,674,241 A | * | 10/1997 | Bley et al. .................. 606/198 |
| 6,019,789 A | * | 2/2000 | Dinh et al. ................ 623/1.15 |
| 6,168,619 B1 | * | 1/2001 | Dinh et al. ................ 623/1.13 |

* cited by examiner

Primary Examiner—Tatyana Zalukaeva
(74) Attorney, Agent, or Firm—Pennie & Edmonds LLP

(57) ABSTRACT

A stent for insertion into a lumen, having rigid regions and flexible regions along its length, and one or more polymer members coaxially disposed about the outer surface of the stent The polymer members are positioned over the rigid regions of the support stent, while the flexible regions are uncovered and free of polymer members, wherein the polymer members are radially expandable with the support stent.

17 Claims, 5 Drawing Sheets

INTRALUMINAL STENT HAVING COAXIAL POLYMER MEMBER

This application is a division of U.S. application Ser. No. 09/335,438 filed Jun. 17, 1999, now abandoned which claims the priority of U.S. provisional application Ser. No. 60/115,609, filed Jan. 12, 1999, which are both incorporated herein by reference.

FIELD OF THE INVENTION

The present invention relates to polymer compositions for use in forming a stent for insertion into a body lumen. A stent having a polymer sleeve formed of the disclosed compositions is also described.

BACKGROUND OF THE INVENTION

Endoluminal stents, particularly endovascular stents, are of considerable interest in the medical profession, especially to vascular surgeons. Such stents are presently used as a post-angioplasty adjunct to maintain the angioplasty-treated blood vessel in an open condition. Examples of endoluminal stents in the art include pressure-expandable stents which radially expand using a balloon angioplasty catheter, such as the Palmaz stent in U.S. Pat. No. 4,733,665; or self-expanding stents which radially expand due to the inherent spring tension of a wire material, such as the stent described by Gianturco in U.S. Pat. No. 4,580,568. Self-expanding stents which expand upon application of a stimulus, such as Nitinol stents or shape-memory polymer stents that expand when exposed to an increase in temperature, have also been described (Froix, U.S. Pat. No. 5,163,952).

In some applications it is desirable to cover the stent with a biocompatible material, since the stents themselves are often thrombogenic and the open nature of the stents can result in growth of tissue through the stent and into the lumen causing occlusion. It has also been desirable in some applications, and in particular for applications employing a metal stent, to provide a means for delivery of a therapeutic agent at the site of stent placement. One approach to meeting these desires has been to provide a polymer sleeve or sheath over the metal stent.

For example, in U.S. Pat. No. 5,674,241 to Bley et al. is described an expandable support stent having an expandable polymer layer coupled to the support stent. The expandable polymer layer is hydrophilic and expands upon hydration.

In U.S. Pat. No. 5,707,385 to Williams an expandable membrane having a drug reservoir is described. The membrane is mounted on the outer surface of a stent and the membrane-covered stent is delivered intraluminally to an injured or diseased site using a balloon-inflatable catheter.

U.S. Pat. No. 5,383,928 to Scott et al. discloses a sheath which encompasses a stent. The sheath serves as a local drug delivery device to prevent thrombosis and/or restenosis.

In U.S. Pat. No. 5,637,113 to Tartaglia et al. there is described an expandable stent structural member having a planar sheet of polymeric material attached to the outside of the structural stent member.

However, the polymer-stent combinations described heretofore in the art have a variety of shortcomings. For example, some polymer sheaths covering a metal support stent result in a significant reduction of flexibility and tractability of the stent, making deployment into a peripheral vascular network difficult. The reduction in flexibility and tractability also makes access past tortuous portions of a vessel difficult or impossible. Polymer membranes that are thick enough to carry a sufficient drug load can require a large balloon pressure to expand the stent and the coextensive polymer membrane into its open state. Large balloon pressures are undesirable for safety reasons. Thick polymer members also increase the profile of the overall stent limiting access to distal portions of the vessel. Additionally, many of the polymer membranes and sheaths axially shorten with radial expansion, leaving the ends of the metal stent uncovered.

There are other problems associated with polymer sleeves described in the art. Because the polymer sleeves are expanded to fit into a lumen, they are often made from a material having some elasticity. The polymer sleeve needs sufficient elasticity for expansion and for a snug fit about the support stent prior to expansion, but should exert little restoring force after expansion. Many polymer sleeves after expansion exert a recovery force on the support stent, preventing the stent from remaining in its fully expanded state, and in the worst cases, can cause the support stent to collapse. Most often the recovery force exerted by the polymer sleeve or member causes the stent to partially recoil, thereby causing obstruction in the vessel lumen and setting up conditions that lead to thrombosis. On the other hand, if the polymer sleeve has insufficient elasticity, the sleeve can drape or sag through openings in the support stent after expansion in a lumen. This disrupts blood flow in the lumen and in severe cases reduces flow to a dangerous level or actually block blood flow altogether.

Also described in the art are polymer sleeves having no elasticity but which are wrapped or folded along the long axis of a support stent. Sufficient polymer material is wrapped about the support stent to allow for expansion from the small stent diameter during placement to the large expanded diameter after deployment. One problem associated with such polymer sleeves is in determining the amount of material needed to provide a uniform covering about the vessel lumen after expansion. To do this with any accuracy, the inner diameter of the target site lumen must be known, which is not always the case. Further, these polymer sleeves, because they are multiply wrapped about the support stent, often bunch-up during tracking to reach the target site, particularly when vessels having a smaller diameter than the target vessel must be navigated.

Accordingly, there is a need in the art for a polymer member designed to be carried on a support stent which overcomes these and other shortcomings.

SUMMARY OF THE INVENTION

In one aspect, the invention includes a composition for use in forming a polymeric stent for insertion into a vessel. The composition is composed of between 10–98% of a first monomer composed of an aliphatic ester C1–C50 of acrylic acid which when homopolymerized has a glass transition temperature lower than about 25° C.; and a second monomer having sites of unsaturation and capable of copolymerization with the first monomer, the second monomer when homopolymerized having a glass transition temperature greater than 25° C. The monomers when polymerized in the presence of a crosslinker form a polymer having a glass transition temperature of less than about 25° C.

In one embodiment, the first monomer is an aliphatic ester of acrylic acid. The first monomer, in another embodiment, is fluorinated. For example, the first monomer is selected from butyl acrylate and pentafluoropropylacrylate.

The second monomer is an ester of methacrylic acid or an ester of acrylic acid. For example, the second monomer is selected from methylmethacrylate, isobornyl methacrylate, isobutyl methacrylate, perfluoroacetylmethacrylate, perfluorobutylmethacrylate, tertiary butylmethacrylate, phenylethylmethacrylate, styrene, hydroxyethyl methacrylate, glycerol methacrylate, n-vinyl pyrrolidone and heptadecylfluorodecyl-methacrylate.

In another embodiment, the polymer composition further includes a third monomer of a methacrylic acid ester or an acrylic acid ester of polyethyleneoxide, where the ester side chain has a molecular weight of between 200–10,000 Daltons. For example, the third monomer is selected from polyethyleneglycol dimethacrylate, polyethyleneglycol methacrylate and polyethyleneglycol acrylate.

One preferred polymer is where the first monomer is butyl acrylate, the second monomer is methylmethacrylate and the third monomer is polyethylene glycol methacrylate. Another preferred polymer is where the first monomer is pentafluoropropylacrylate and the second monomer is heptadecylfluorodecyl methacrylate. Yet another preferred composition is where the first monomer is pentafluoropropylacrylate and the second monomer is methylmethacrylate and the third monomer is polyethylene glycol methacrylate.

The polymer composition are preferably formed into a stent, which carries a therapeutic agent.

In another aspect, the invention includes a composition for use in forming a polymeric stent for insertion into a vessel, comprising (a) greater than about 40 weight percent of butyl acrylate monomer; (b) between 3–30 weight percent of methylmethacrylate monomer; (c) between 2–40 weight percent of polyethylene glycol methacrylate monomer or polyethyleneglycol monomethyl ether monomethacrylate. The composition when polymerized forms a polymer having a glass transition temperature of less than 25° C.

The composition of this aspect includes, in other embodiments, one or more of the following components: (a) between 0.1–20 weight percent of an organic solvent; (b) a monomer effective to impart a charge to the polymer; (c) between 0.025–0.1 weight percent of a crosslinker; and (d) between 0.1–1 weight percent of an initiator, such as a photoinitiator or a thermal initiator. The solvent, for example, can be dimethylformamide in an amount between 1–15 weight percent. The monomer effective to impart a charge is preferably a monomer which at physiologic pH is effective to impart a positive charge, such as dimethylaminoethyl methacrylate. In another embodiment, it is a monomer effective to impart a negative charge at physiologic pH, such as methacrylic acid or acrylic acid. The crosslinker is selected from the group consisting of ethoxylated trimethylolpropane triacrylate and hexanediol dimethacrylate.

In another aspect, the invention includes a composition for use in forming a polymeric stent for insertion into a vessel, comprising (a) greater than about 40 weight percent of pentafluoropropyl acrylate monomer; and (b) between 3–30 weight percent of (heptadecyl fluorodecyl methacrylate) monomer. The composition when polymerized forms a polymer having a glass transition temperature of less than 25° C.

In another aspect, the invention includes a composition for use in forming a polymeric stent for insertion into a vessel, comprising (a) greater than about 40 weight percent of pentafluoropropyl acrylate monomer; (b) between 3–30 weight percent of polyethylene glycol methacrylate monomer or polyethyleneglycol monomethylether methacrylate monomer; and (c) between 2–40 weight percent of methylmethacrylate monomer. The composition when polymerized forms a polymer having a glass transition temperature of less than 25° C.

In still another aspect, the invention includes a stent for insertion into a lumen, comprising a radially expandable, support stent having a selected axial length and an outer surface, the stent having rigid regions and flexible regions along its length. The stent includes one or more polymer members coaxially disposed about the outer surface of the support stent, the polymer members positioned over the rigid regions of the support stent, with the flexible regions exposed, and the polymer members being radially expandable with the support stent.

In an embodiment of this aspect, the polymer members are composed of (i) between 10–98% of a first monomer composed of an aliphatic ester C1–C50 of acrylic acid which when homopolymerized has a glass transition temperature lower than about 25° C.; and (ii) a second monomer having sites of unsaturation and capable of free radical polymerization, the second monomer when homopolymerized having a glass transition temperature greater than 25° C., the monomers when polymerized in the presence of a crosslinker forming a polymer having a glass transition temperature of less than about 25° C.

In a preferred embodiment, the stent further includes a therapeutic agent.

One preferred stent composition is where the polymer members are composed of (a) greater than about 40 weight percent of butyl acrylate monomer; (b) between 3–30 weight percent of methylmethacrylate monomer; (c) between 2–40 weight percent of polyethylene glycol monomethylether monomethyacrylate. The monomers when polymerized form a copolymer having a glass transition temperature of less than 25° C.

In another aspect, the invention includes a stent for insertion into a lumen. The stent is composed of (i) a radially expandable, support stent having a selected axial length and an outer surface; the stent having rigid regions and flexible regions along its length; and (ii) one or more polymer members coaxially disposed about the outer surface of the support stent. The polymer members are positioned over the rigid regions of the support stent, with the flexible regions exposed, and the polymer members are radially expandable with the support stent. The polymer members are composed of (a) greater than about 40 weight percent of pentafluoropropyl acrylate monomer; and (b) between 3–30 weight percent of (heptadecyl fluorodecyl methacrylate) monomer. The monomers when polymerized form a polymer having a glass transition temperature of less than 25° C.

In another aspect, the invention includes a stent for insertion into a lumen as described above, where the polymer members are composed of (a) greater than about 40 weight percent of pentafluoropropyl acrylate monomer; (b) between 3–30 weight percent of polyethylene glycol methacrylate monomer or polyethylene glycol monomethylether monomethyacrylate; and (c) between 2–40 weight percent of methylmethacrylate monomer. The monomers when polymerized form a polymer having a glass transition temperature of less than 25° C.

These and other objects and features of the invention will be more fully appreciated when the following detailed description of the invention is read in conjunction with the accompanying drawings.

DETAILED DESCRIPTION OF THE INVENTION

I. Definitions

"Acrylate monomer" as used herein refers to a monomer capable of forming a polymer of acrylic acid or its esters and having the general structure —(CH$_2$—CH(COOR))$_n$—. The R group is typically a group having between 1–50 carbon atoms, more preferably between 1–20 carbon atoms.

"Acrylate" or "acrylate polymer" refers to a polymer, usually a copolymer, prepared from an acrylate monomer.

"Methacrylate monomer" as used herein refers to a monomer for formation of a polymer of methacrylic acid or its esters with a —(CH$_2$—C(CH$_3$)(COOR))$_n$— structure. The R group is typically a group having between 1–50 carbon atoms, more preferably between 1–20 carbon atoms.

"Methacrylate" or "methacrylate polymer" refers to a polymer, usually a copolymer, prepared from a methacrylate monomer.

"Polyalkyleneoxide" refers to a polymer having the general structure R$^1$(OCH$_2$(CHR$^2$OCHR$^3$)CH$_2$O)$_n$R$^4$, where the R$^2$ and R$^3$ can be H or a C1–C$_{10}$ alkane, and the end groups R$^1$ and R$^4$ can be H or any suitable end moiety, such as CH3 to give a methoxy, or various ethers. Exemplary polyalkyleneoxides include polyethylene oxide (polyethylene glycol), polyethylene oxide monomethyl ether monomethacrylate, polypropylene glycol.

"Polymer" as used herein refers to homopolymers and copolymers, including random, alternating and block copolymers.

II. Polymer Compositions

The polymer compositions of the present invention are preferably for use in forming a stent for use in maintaining vessel patency and/or reducing restenosis. The stent formed from the compositions is preferably of the type carried coaxially about the outer circumference of a support stent, and examples of this will be described below. However, it will be appreciated that the compositions may find use in forming not only support stents or polymer sleeves for use with a support stent, but in other medical devices.

Figure 1A:
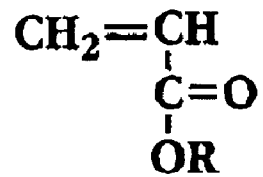
FIGS. 1A–1D show the general monomer structures for an ester of acrylic acid (FIG. 1A), an ester of methacrylic acid (FIG. 1B), butyl acrylate (FIG. 1C) and pentafluoropropylacrylate (FIG. 1D)
Figure 1B:
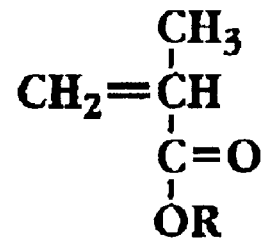
Figure 1C:
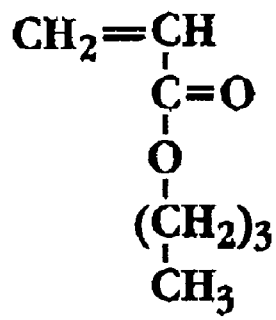
Figure 1D:
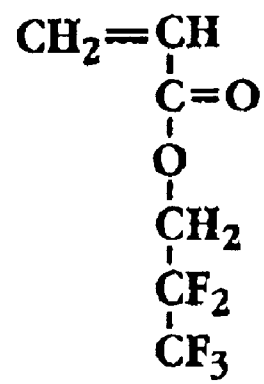

The polymer compositions of the invention include as a first component, a monomer that is an aliphatic ester of acrylic acid or methacrylic acid. The general monomer structure for an ester of acrylic acid is shown in FIG. 1A and for methacrylic acid in FIG. 1B. The monomer when homopolymerized has a backbone of a (—CH$_2$—CX—)$_n$ repeat unit, where X is H or CH$_3$, and where R in the ester side chain (see FIGS. 1A, 1B) can be C1–C50, preferably a C1–C20 group, more preferably, a C1–C10 group, even more preferably a C2–C20, still more preferably C2–C10 group. The aliphatic R group can, in some embodiments, be fluorinated. Some preferred exemplary aliphatic esters of acrylic acid for use in the present invention include butyl acrylate (R=C4) and pentafluoropropylacrylate (R=C3F5), the monomers of which are shown in FIGS. 1C–1D, respectively.

Figure 2:
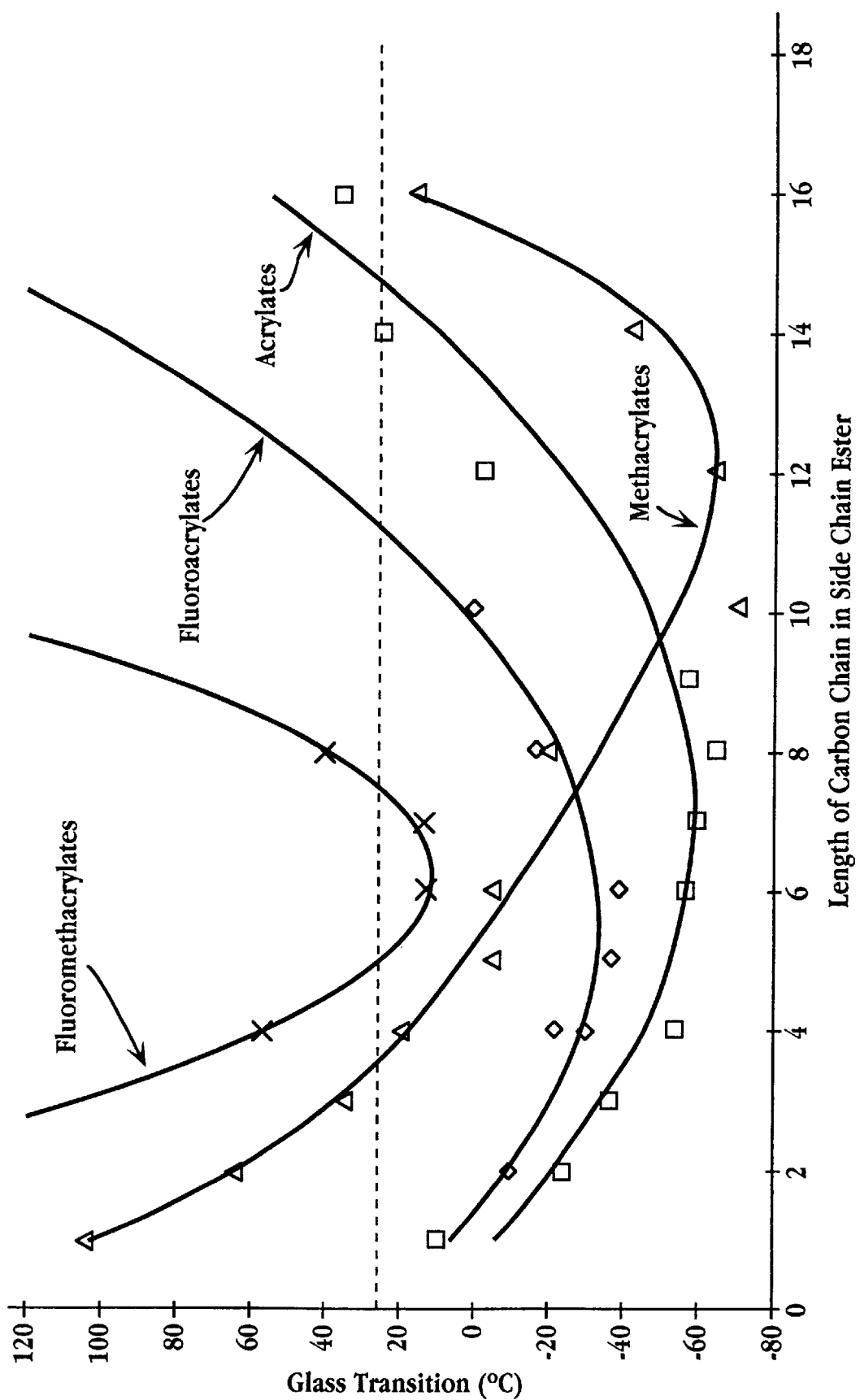
FIG. 2 is a plot showing the glass transition temperature, in ° C., for homopolymers of esters of acrylic acid (open squares) and methacrylic acid (open triangles), where the R group in the side chain esters vary from 1–16 carbons. Also shown in FIG. 2 are the glass transition temperatures for homopolymers of fluoroacrylates (open diamonds) and fluoromethacrylates (X symbols), where the fluorinated R m group in the alcohol portion of the side chain ester varies from between about 2–10 carbon atoms.

According to an important feature of the composition, the first monomer when homopolymerized has a glass transition temperature of less than about 25° C. FIG. 2 is a plot showing the glass transition temperature, in ° C., for homopolymers of acrylic acid (open squares) and methacrylic acid (open triangles), where the R group in the side chain esters vary from 1–16 carbons. Also shown in FIG. 2 are the glass transition temperatures for homopolymers of fluoroacrylates (open diamonds) and fluormethacrylates (X symbols), where the fluorinated R group in the alcohol portion of the side chain ester varies from between about 2–10 carbon atoms. As seen in the figure, a number of monomers are suitable for use as the first monomer in the present invention—namely, any of the monomers which form a homopolymer having a glass transition temperature of less than about 25° C. A dashed line is drawn in FIG. 2 at 25° C., and all the monomers forming the polymers below the dashed line are suitable. More specifically, acrylic acid monomers (open squares) having a side chain in the alcohol portion of the ester with 1, 2, 3, 4, 5, 6, 7, 8, 9, 10, 11 and 12 carbon atoms have glass transition temperatures of less than 25° C. Homopolymers from methacrylic acid monomers (open triangles) having a side chain of C4–C16 all have glass transition temperatures of less than 25° C. Fluoroacrylate homopolymers with a glass transition temperature of less than 25° C. are shown in FIG. 2 (open diamonds) and include those with fluorinated carbon chains in the ester group of at least between 1–10 carbon atoms. Fluoromethyacrylate homopolymers with a glass transition temperature of less than 25° C. (X symbols) include those with fluorinated carbon chains in the ester group having 6 and 7 carbon atoms.

The first monomer is included in the composition of the invention in an amount between 10–98 weight percent, more preferably between 20–95 weight percent, and even more preferably between 40–95, even still more preferably at between about 50–95 weight percent.

The polymers shown in FIG. 2 having glass transition temperatures greater than 25° C. are suitable for use as the second monomer. More generally, the second component of the composition of the invention includes a monomer having sites of unsaturation and which is capable of free radical polymerization and which, when homopolymerized, has a glass transition temperature of greater than 25° C. Clearly, the monomers forming the homopolymers with glass transition temperatures of greater than 25° C. set forth in FIG. 2 fit these requirements, and there are other monomers as well. In studies conducted in support of the invention, monomers of methacrylic acid and aliphatic esters of methacrylic acid were used. Other suitable second monomers include methylmethacrylate, isobornyl methacrylate, isobutyl methacrylate, octadecyl methacrylate, hexyl methacrylate, butyl methacrylate, tertiary butylmethacrylate, phenylethylmethacrylate, and heptadecylfluorodecylmethacrylate.

The amount of second monomer included in the composition depends on the first monomer. According to another important feature of the invention, the first and second monomers, when copolymerized, form a copolymer having a glass transition temperature of less than 25° C. or where at least one block in the copolymer has a glass transition temperature of less than 25° C. That is, the copolymer may exhibit one or more glass transition temperatures, and at least one of the a glass transition temperatures, typically that corresponding to the "soft" block, should be less than 25° C. Formation of the copolymer is preferably by step copolymerization to achieve preferably, an alternating copolymer, however, random and block (diblock, triblock, etc.) copolymers are also contemplated. Copolymerization of the two monomers to form a random copolymer results when the monomer reactivity ratios $r_1$ and $r_2$, defined as the ratios of the rate constant for a given radical adding its own monomer to the rate constant for its adding the other monomer, show the same preference for adding one of the monomers over the other, that is $r_1 r_2 = 1$. In this case, the end group on the growing chain has no influence on the rate of addition, and the two types of monomer units are arranged at random along the chain in relative amounts determined by the composition of the feed and the relative reactivities of the two monomers. An alternating copolymer is formed where each monomer radical prefers to react exclusively with the other monomer radical, e.g., $r_1 = r_2 = 0$. The monomers alternate regularly along the chain, regardless of the composition of the monomer feed. Block copolymers form when $r_1$ and $r_2$ are both greater than unity, indicating that each monomer radical prefers to react with a monomer radical of its own type.

The glass transition temperatures of copolymers, more specifically for random copolymers, usually falls between those of the corresponding homopolymers, where the glass transition of the copolymer is often estimated as a weighted average according to $a_1 w_1 (Tg - Tg^1) + a_2 w_2 (Tg - Tg^2) = 0$, where $Tg^1$ and $Tg^2$ refer to the glass transition temperature of the homopolymers, $w_1$ and $w_2$ are weight fractions of monomers 1 and 2 in the copolymer and $a_1$ and $a_2$ depend on the monomer type and are given by Wood, L., *J. Polymer. Sci.* 28:319 (1958). Another equation for estimating the glass transition temperature of copolymers of known monomer composition is using the equation $$1/Tg = w_1/Tg^1 + w_2/Tg^2 + w_3/Tg3 + w_n/Tg^n.$$

Thus, the amount of the second monomer will be dependent on the selection of the first monomer and the reaction conditions, but in accordance with the invention, the amount of the second monomer is selected to obtain a copolymer between the first monomer and the second monomer that has a glass transition temperature of less than about 25° C.

Glass transition temperatures are readily measured by a variety of methods, including those methods dealing with bulk polymer properties and those measuring the nature and extent of molecular motions. One common way to measure Tg is by means of thermal analysis, either differential scanning calorimetery or differential thermal analysis. Other methodologies include volume expansion coefficient, NMR spectroscopy and refractive index.

In some embodiments of the invention, the polymer composition includes a third monomer capable of copolymerization with the first and/or second monomers. The third monomer is a methacrylic acid ester of polyethyleneoxide or an acrylic acid ester of polyethyleneoxide, and in preferred embodiments is selected from polyethyleneglycol methacrylates and polyethyleneglycol acrylates. Preferred third monomers include polyethyleneglycol dimethacrylates and polyethyleneglycol diacrylates.

In studies conducted in support of the invention, a variety of polymer compositions were prepared, as will now be described with respect to Tables 1–6.

As described in Example 1, the exemplary copolymers were prepared by mixing the indicated monomers, crosslinker and photoinitiator and placing the mixture into a clear mold. Polymerization was initiated by exposing the mixture to UV light. The polymerized article was removed from the mold for analysis. It will be appreciated that a variety of methods are suitable for polymerization of the desired mixtures. For example, the monomers can be polymerized in a batch reactor in the absence of a crosslinker. The polymer is pelleted for feeding along with the crosslinker and UV initiator or thermal initiator through an extruder to provide a continuous length of tubing. The tubing is exposed to UV light for crosslinking and then cut into suitable lengths to provide a stent.

A polymer composition in accordance with the invention was prepared using as the first monomer pentafluoropropyl acrylate and as the second monomer heptadecylfluorodecylmethacrylate. The amount of the monomers and the crosslinker (Darocure® 1173) and UV initiator (hexanediol dimethacrylate) are given in Table 1.

TABLE 1

| Component | Weight percent |
| --- | --- |
| pentafluoropropyl acrylate | 74.8 |
| heptadecylfluorodecyl methacrylate | 25.0 |
| Darocure ® 1173 | 0.12 |
| hexanediol dimethacrylate | 0.05 |
| Tg (° C.) | 2 |
| secant modulus (psi) | 20.1 ± 3.8 |
| strain @ break | >950% |

The copolymer formed was characterized for tensile properties according to the procedure set forth in Example 2, and the secant modulus and strain at break are given in the table. The glass transition temperature of the polymer was 2° C. The Tg values were calculated using the equation given above.

A second exemplary polymer composition was prepared using pentafluoropropyl acrylate as the first monomer, methylmethacrylate as the second monomer and polyethyleneglycol monomethyl ether monomethacrylate (molecular weight 1000 Daltons) as the third monomer in the amounts set forth in Table 2.

TABLE 2

| Component | Weight percent |
| --- | --- |
| pentafluoropropyl acrylate | 69.91 |
| polyethyleneglycol monomethyl ether monomethacrylate (MW 1000) | 25.05 |
| methylmethacrylate | 4.86 |
| Darocure ® 1173 | 0.12 |
| hexanediol dimethacrylate | 0.06 |
| Tg (° C.) | −16 |
| secant modulus (psi) | 0.4 ± 0.1 |
| strain @ break | 557 ± 51% |

The copolymer was characterized for tensile properties according to the procedure set forth in Example 2, and the secant modulus and strain at break are given in the table. The glass transition temperature of the polymer was −16° C.

A third exemplary copolymer was prepared using butyl acrylate as the first monomer, methylmethacrylate as the second monomer and polyethyleneglycol monomethyl ether monomethacrylate (molecular weight 1000 Daltons) as the third monomer in the amounts set forth in Table 3.

TABLE 3

| Component | Weight percent |
| --- | --- |
| butyl acrylate | 60.02 |
| polyethyleneglycol monomethyl ether monomethacrylate (MW 1000) | 14.99 |
| methylmethacrylate | 24.83 |
| Darocure ® 1173 | 0.10 |
| hexanediol dimethacrylate | 0.06 |
| Tg (° C.) | −10 |
| secant modulus (psi) | 23.4 ± 1.5 |
| strain @ break | 640 ± 69% |

The copolymer was characterized for tensile properties according to the procedure set forth in Example 2, and the secant modulus and strain at break are given in the table. The glass transition temperature of the polymer was −10° C.

Another exemplary copolymer was prepared using the same monomers as the copolymer in Table 3, but in different proportions, as set forth in Table 4. The copolymer in Table 4 also includes dimethylformamide added to the monomer mixture prior to polymerization.

TABLE 4

| Component | Weight percent |
| --- | --- |
| butyl acrylate | 60.06 |
| polyethyleneglycol monomethyl ether monomethacrylate (MW 1000) | 29.96 |
| methylmethacrylate | 9.83 |
| Darocure ® 1173 | 0.10 |
| ethoxylated trimethylolpropane triacrylate | 0.05 |
| dimethylformamide | 9.10 |
| Tg (° C.) | −30 |
| secant modulus (psi) | 4.7 ± 0.4 |
| strain @ break | 554 ± 55% |

The copolymer was characterized for tensile properties according to the procedure set forth in Example 2, and the secant modulus and strain at break are given in the table. The glass transition temperature of the polymer was −30° C.

Table 5 sets forth the components of another exemplary copolymer. In this example, added to the first, second and third monomer, was a monomer capable of being quaternized to a cationic monomer, dimethylaminoethylmethacrylate.

TABLE 5

| Component | Weight percent |
| --- | --- |
| butyl acrylate | 59.98 |
| polyethyleneglycol monomethyl ether monomethacrylate (MW 1000) | 25.00 |
| methylmethacrylate | 12.86 |
| dimethylaminoethylmethacrylate | 2.00 |
| Darocure ® 1173 | 0.10 |
| hexanediol dimethacrylate | 0.06 |
| Tg (° C.) | −24 |
| secant modulus (psi) | 5.1 ± 0.2 |
| strain @ break | 606 ± 34% |

The copolymer was characterized for tensile properties according to the procedure set forth in Example 2, and the secant modulus and strain at break are given in the table. The glass transition temperature of the polymer was −24° C.

Table 6 sets forth the components of another exemplary copolymer. In this example, added to the first, second and third monomers was methacrylic acid monomer. The methacrylic acid monomer is capable of being ionized to an anionic monomer, to add charge to the resulting copolymer.

TABLE 6

| Component | Weight percent |
| --- | --- |
| butyl acrylate | 51.5 |
| polyethyleneglycol monomethyl ether monomethacrylate (MW 400) | 40.0 |
| methylmethacrylate | 4.85 |
| methacrylic acid | 2.00 |
| Darocure ® 1173 | 0.10 |
| hexanediol dimethacrylate | 0.05 |
| Tg (° C.) | −37 |
| secant modulus (psi) | 6.6 ± 0.2 |
| strain @ break | 443 ± 32% |

The copolymer was characterized for tensile properties according to the procedure set forth in Example 2, and the secant modulus and strain at break are given in the table. The glass transition temperature of the polymer was −37° C.

The polymers of the invention, as exemplified by those described in Tables 1–6, have glass transition temperatures below 25° C. This property is an important feature of the invention, as it provides an elastomeric polymer capable of expanding readily by means of a balloon catheter. Polymers having a glass transition temperature above 25° C. are often not sufficiently elastic at body temperature (approximately 37° C.) to readily expand with little to no recoil.

The secant modulus at 100% strain and the strain at break of the copolymer prepared in support of the invention was determined (Example 2), as noted above with respect to Tables 1–6, which provide an indication of the elasticity and stiffness of the copolymers. The secant modulus was taken as the slope of the line drawn between the point on the stress-strain curve at 100% strain and the origin. The secant modulus provides a measure of the stiffness of the polymer, which a high secant modulus characteristic of materials which recoil after elongation with great force. For purposes of the present invention, it is desired to have a material with a secant modulus that is equal to or less than the force required to collapse the supporting metal stent over which a polymer member prepared from the material is made. For example, if a force of 15 psi is required to cause the support stent to collapse, then a copolymer having a secant modulus equal to or less than 15 psi for preparation of the polymer member is desired. It will be appreciated that the force required to collapse the metal stent varies according to the configuration of the stent and the material from which the stent is made. This variation in force allows for variation in the required secant modulus of the copolymer for formation of the polymer member. The secant modulus of the polymers ranges from 0.4 psi (polymer of Table 2) to 23 psi (polymer of Table 3). The polymers of the invention, thus, can be characterized as those having a secant modulus of less than 50 psi, more preferably of less than 30 psi, and even more preferably of between 0.1–30 psi. The secant modulus for polymer members used in combination with larger stents, such as those for use in the aorta, where the stent expands from, for example 5 mm to 30 mm in diameter, can be greater than 50 psi.

The strain at break provides an indication of the elasticity of the copolymer, by determining how much stress can be applied before the material breaks. This is important since the polymer member must be able to stretch with the support stent from a small diameter condition during insertion and placement of the stent in a vessel to a large diameter condition after deployment in the vessel. Depending on the size of the target vessel, the stent and the polymer member may need to stretch 100–600%. The strain at break of the polymers ranges from 443% (Table 6) to >950% (Table 1). More generally, the copolymers prepared in support of the invention have a strain at break of greater than 400%, with most having a strain at break of greater than 500%, and many with a strain at break of greater than 600%. The polymers of the invention are those having a strain at break of greater than about 100%, more preferably greater than 250%, and most preferably greater than 500%.

In the copolymers described in Tables 5 and 6, the polymer composition includes a monomer effective to impart a charge to the copolymer at physiologic pH. The monomer can be one that at physiologic pH ionizes to either a positive charge, such as the monomer dimethylaminoethylmethacrylate, or a negative charge, such as the methylacrylic acid.

In another embodiment, the copolymer includes a solvent. The solvent is typically added to the monomer mixture during polymerization, and exemplary solvents include dimethylformamide, isopropylalcohol, ethanol and dimethylsulfoxide. Other solvents having an affinity for the polymer and which meet accepted toxicology requirements are also suitable.

Polymer members prepared in accordance with the invention have been used for in vivo insertion into vessels. The polymer members were loaded with a therapeutic agent and placed over a metal support stent. The stent/polymer member were inserted into the target lumen using a balloon catheter according to standard practice. Stents without the polymer members were inserted for controls. Stents having the polymer member were found to tract and deploy as easily as the control stents, and the polymer member caused no additional recoil of the metal support stent after expansion and removal of the balloon catheter.

III. Stents Formed from the Polymer Compositions

In another aspect, the invention includes a stent for insertion into a lumen. The stent includes a support stent which is radially expandable and a polymer member, prepared from a polymer composition as described above, carried coaxially about the outer surface of the support stent.

Most generally, the stent of this aspect of the invention includes a support stent which is a metal or polymer stent, as are widely known in the art, for example metallic stents composed of biocompatible metals such as nickel-titanium alloys and stainless steel. Such metal support stent vary considerably in their geometric form, but are all suitable for implantation into a body lumen in a collapsed or small-diameter condition and for expansion to a larger diameter condition upon placement at the site to be treated. Stents known in the art and suitable for use in the present invention include pressure-expandable stents, self-expanding stents and stents which expand in response to an applied stimulus, such as heat. An exemplary pressure-expanding stent is described in U.S. Pat. Nos. 4,776,337 and 4,733,665 to Palmaz. Pressure-expandable stents are typically radially expanded by means of a balloon angioplasty catheter, as is known in the art. Self-expanding stents, such as the stent described by Gianturco in U.S. Pat. No. 4,580,568 and by Wallsten in U.S. Pat. No. 4,544,771, radially expand due to the inherent spring tension of the stent. The stents expand to a larger diameter after being released from a constraining force which restricts it to a smaller diameter. Another sort of self-expanding stent includes stents made of shape-memory material, such as nitinol or shape-memory polymers described by Froix in U.S. Pat. No. 5,163,952.

Figure 3A:
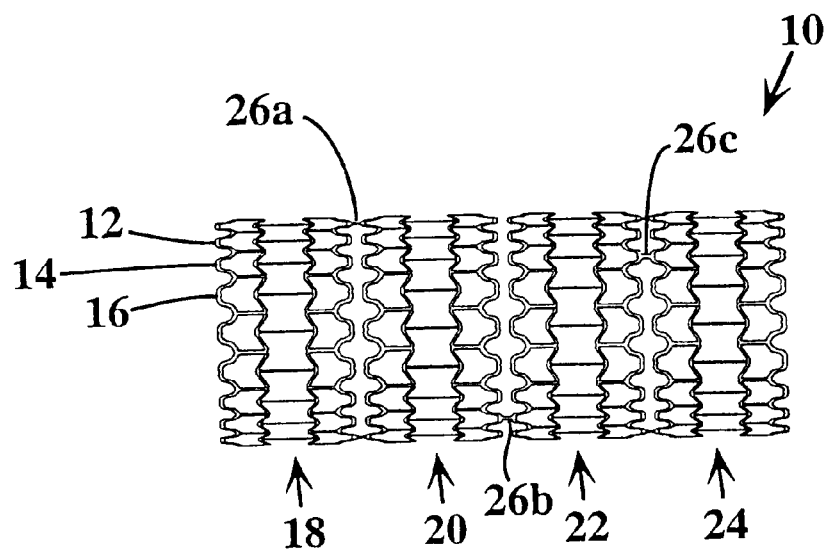
FIGS. 3A–3C show a support stent (FIG. 3A) suitable for carrying a polymer sleeve (FIG. 3B) or polymer members (FIG. 3C) containing a therapeutic agent.

In a preferred embodiment of this aspect, the support stent is one having a selected axial length, along which are more rigid regions separated by more flexible regions. A support stent having this feature is illustrated in FIG. 3A where the metal support stent 10 is shown in an expanded, large diameter condition. The stent is composed of unit cells, such as unit cells 12, 14, 16, joined in a radial direction to form a plurality of unit cells 18. Each unit cell is expandable to move the stent from a small-diameter condition, for insertion into a body lumen, to a large-diameter condition, for deployment into the body lumen. Support stent 10 as shown is composed of four pluralities of unit cells, 18, 20, 22 and 24. The pluralities of unit cells are joined radially by a connecting segment, such as connecting segments 26a, 26b, 26c, which join pluralities 18, 20; 20, 22; and 22, 24, respectively. As can be appreciated, the stent can be composed of any number of pluralities to give any desired stent length, and the dimensions of each unit cell can readily be varied to determine stent length and diameter. The stent in regions which correspond to each plurality of unit cells, is relatively rigid compared to the regions between each plurality and corresponding to the connecting segments. This is an important feature of the stent, since the more flexible regions corresponding to the connecting segments gives better flexibility and tractability to the stent for easier navigation and placement in vessels. The stent of FIG. 3A is described in detail in co-pending application Ser. No. 09/053,887, filed Apr. 1, 1998, which is herein incorporated by reference.

Figure 3B:
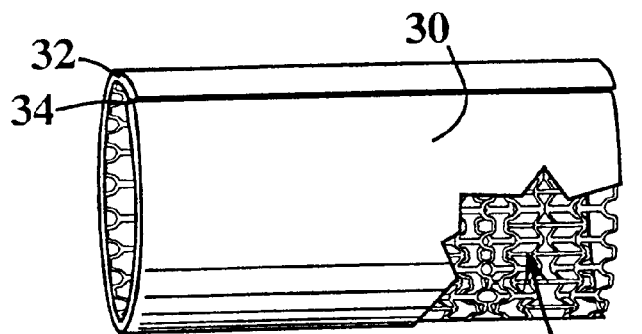

FIG. 3B shows the metal stent of FIG. 3A with a continuous polymer sheath 30 encasing the metal support stent. The outer polymer sleeve is prepared, for example, as set forth in Example 1, and is composed of a polymer composition described above, especially with respect to the compositions set forth in Tables 1–6. The sleeve is carried coaxially about the outer circumference of the support stent and takes the form of a flat sheet rolled into a cylindrical or tubular shape by overlapping the edges 32, 34 of the sheet. It will be appreciated that the initial configuration of the tubular member is not limited to a flat sheet, but can also be prepared from an extruded tube-form or from a molded tube-form.

Figure 3C:
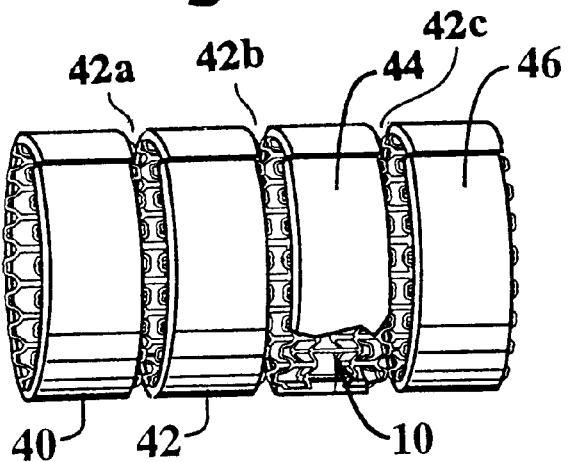

In accordance with another preferred embodiment of this aspect, a stent composed of a support stent having rigid and flexible regions, like that discussed above in FIG. 3A, and carrying one or more polymer members disposed about the rigid stent regions is contemplated. A stent 40 in accordance with this aspect of the invention is illustrated in FIG. 3C, where metal stent 10 of FIG. 3A is shown. Stent 10 has four rigid regions which correspond to the unit cell pluralities 18, 20, 22, 24 (see FIG. 3A). By "rigid" it is meant that in this region of the stent, flexure in the radial direction is minimal, especially when compared to the radial flexure of the regions corresponding to where the connecting segments join the rigid regions. These flexible regions are identified in FIG. 3C as regions 42a, 42b, 42C. In this aspect of the invention, polymer members coaxially about the outer stent surface only in the rigid stent regions, as are polymer members 40, 42, 44 and 46, leaving the flexible regions 42a, 42b, 42c, exposed or uncovered. This positioning of the polymer members offers the advantage of carrying a polymer member for administration of a therapeutic compound, while maintaining the flexibility offered by the articulating stent. It will be appreciated that this configuration of polymer members is useful for polymer members formed from nearly any polymer composition, and where drape and sag of the polymer member into the stent lumen is a problem, the configuration overcomes such issues. Drape and sag of the polymer member occurs in regions where the support stent offers inadequate support, as in the region of flexure. However, as noted above, the polymer compositions described herein are suitable for use as a polymer sleeve covering the stent length, e.g., the FIG. 3B embodiment, as the compositions do not suffer from drape and sag.

Figure 4A:
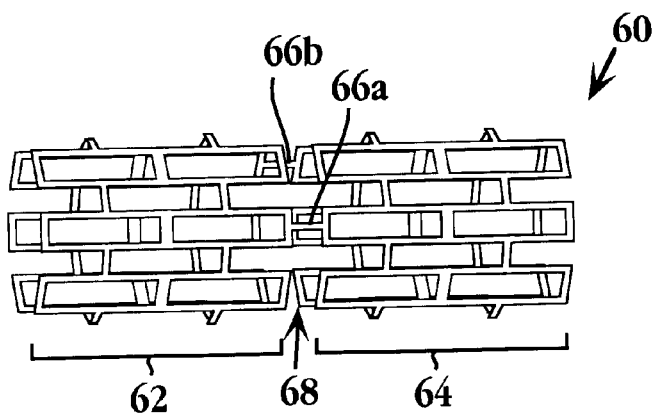
FIGS. 4A–4C illustrate another embodiment of a support stent in its small, unexpanded condition (FIG. 4A) and in its larger diameter, expanded condition (FIG. 4B) which is suitable for carrying polymer members positioned about the rigid support stent regions (FIG. 4C)
Figure 4B:
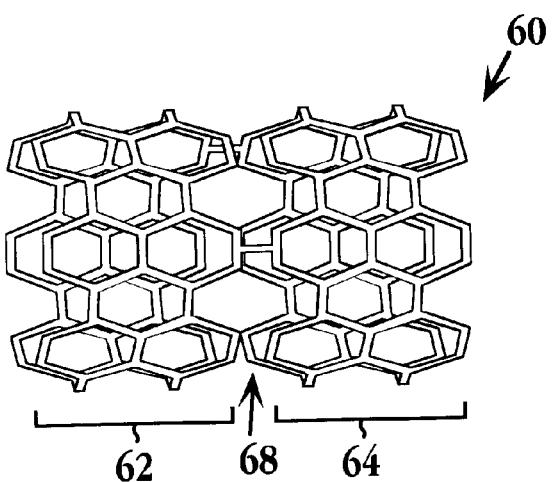
Figure 4C:
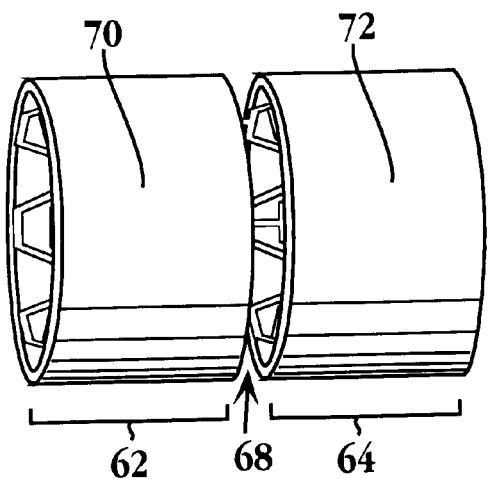

FIGS. 4A–4C illustrate another exemplary support stent suitable for use in this aspect of the invention. A metal support stent 60 is shown in FIG. 4A in its small-diameter, unexpanded condition. Stent 60 has two regions of rigidity, 62, 64, where flexure in the radial direction is minimally possible. The two rigid regions are joined by one or more connecting segments, such as segments 66a, 66b, and define a flexible stent region 68. The same stent is shown in FIG. 4B in its larger f diameter, expanded condition, where the rigid regions 62, 64 and the flexible region 68 are clearly indicated. In accordance with this aspect of the invention, stent 60 includes at least one polymer member disposed about one or more of the rigid stent regions. As shown in FIG. 4C, polymer members 70, 72 cover rigid regions 62, 64, respectively, leaving flexible region 68 uncovered and exposed. In this example, the polymer members take the form of molded cylinders with no overlapping edges, as polymer members formed in a molded or extruded tube-form will have.

Figure 5A:
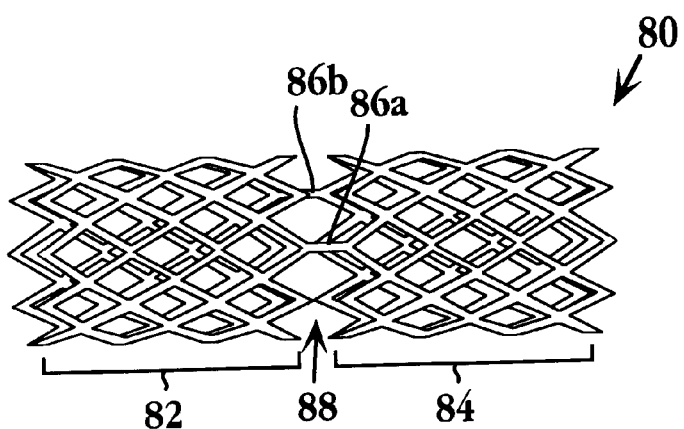
FIGS. 5A–5C illustrate yet another embodiment of a support stent in its small, unexpanded condition (FIG. 5A) and in its larger diameter, expanded condition (FIG. 5B) which is suitable for carrying polymer members about the rigid support stent regions (FIG. 5C).
Figure 5B:
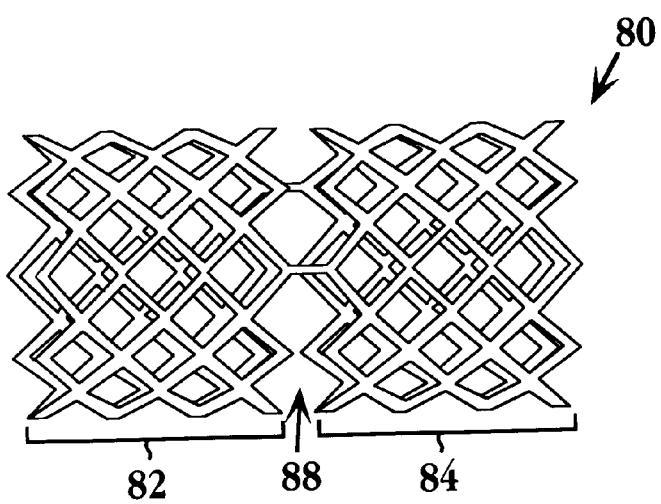
Figure 5C:
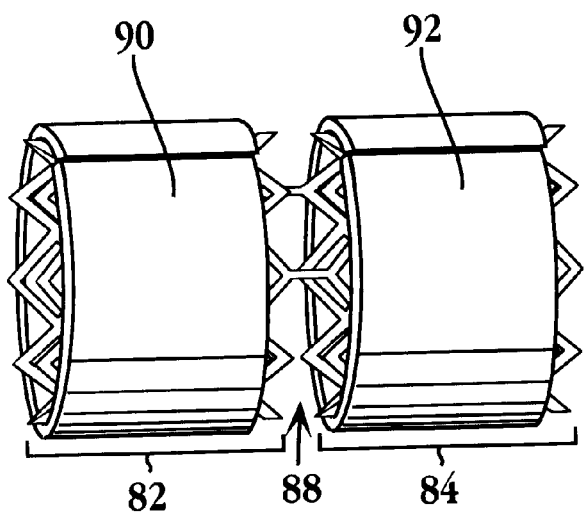

Another example of a support stent with polymer members is illustrated in FIGS. 5A–5C. Here the support stent 80 in its small diameter condition is shown in FIG. 5A where rigid stent regions 82, 84 are joined by one or more connecting segments 86a, 86b, which define a region of flexibility 88. The stent in its large diameter, expanded condition after placement in a vessel is shown in FIG. 5B. The stent with polymer members covering the rigid stent regions is shown in FIG. 5C, where polymer members 90, 92 are positioned over rigid regions 82, 84, respectively.

In all of the embodiment described above, the support stent is composed of a biocompatible materials, and suitable materials include metals, such as stainless steel, tungsten, titanium, gold, platinum and tantalum, alloys of these materials and others, as well as shape-memory alloys, high strength thermoplastic polymers, copolymers, including shape-memory polymers. Shape-memory copolymers including homopolymers and copolymers are contemplated.

The polymer members are composed of, in addition to the compositions described herein, any biocompatible polymer, such as polyamides, polyimides, silicones and fluorinated polyolefins. The polymer member is formed into a tubular configuration, either by extrusion or molding directly into a cylindrical form or by wrapping a polymer sheet into a cylindrical configuration. The polymer members can be self-securing by appropriate sizing of the inner diameter of the member or the polymer members are secured in an unexpanded diameter to the support stent by a mechanical means, such as by ultrasonic welding, resistive heating and laser irradiation. Alternatively, the polymer tubular member is secured to the support stent in an unexpanded diameter by a biocompatible adhesive, such as a fluorinated thermoplastic polymer adhesive. Examples of fluorinated thermoplastic include fluorinated ethylene/propylene copolymers, perfluoroalkoxy fluorocarbons, ethylene/tetrafluoroethylene copolymers, fluoroacrylates, and fluorinated polyvinyl ethers. Biological adhesives such as heparin, collagen and fibrin are also suitable. It is also possible that the polymer member has sufficient inherent elasticity to remain secured to the support stent in its small, unexpanded diameter with no adhesive.

The polymer members are intended for administration of a therapeutic compound at the target site. The therapeutic compound can be loaded into the polymer member prior to or after fabrication. For example, a therapeutic agent can be added to the monomer mixture, or the drug in a suitable solvent can be imbibed into the preformed stent. Other methods of loading the agent into the polymer member are apparent to those of skill in the art.

It will be appreciated that the polymer member(s) can include virtually any therapeutic agent. Therapeutic agents contemplated for use include, but are not limited to, agents effective to inhibit or reduce smooth muscle proliferation and/or agents effective to inhibit or reduce proliferation or migration of fibroblast cells. Examples of such agents include paclitaxel and its derivatives, colchicine and DNA oligonucleotides, such as those oligonucleotides described in WO 98/23229. Other exemplary agents include anticoagulants, antiplatlet agents and antibacterial agents. Specific preferred agents include heparin, methotrexate, rapamycin, warfarin, low molecular weight heparin, hirudin, glucocorticoids, angiotensin converting enzyme inhibitors, vincristine, actinomycin, and platelet derived growth factor. Another preferred group of agents is topoisomerase inhibitors, including compounds having activity against topoisomerase I and topoisomerse II enzymes as well as agents having combined activity against both topoisomerase I and II. A preferred topoisomerase I inhibitor is camptothecin and analogues of camptothecin. Other contemplated agents include vascular endothelial growth factor (VEGF), thrombolytic agents, such as streptokinase, urokinase, and tissue plasminogen activator (TPA).

In another embodiment of the invention, the polymer members carries two therapeutic agents. For example, the first agent is paclitaxel or a derivative of paclitaxel and the second agent is any of those recited above, such as camptothecin, colchicine or dexamethasone.

EXAMPLES

The following examples set forth methods for preparing and characterizing the polymer compositions of the present invention. The examples are intended to by illustrative and in no way limit the scope of the invention.

Example 1

Copolymer Preparation

The monomers, crosslinker and UV initiator were mixed and then introduced into a transparent mold. The mold for formation of a stent was formed from two coaxial tubes of Teflon® separated by tubular gaskets at each end. The inner tube size was selected according to the desired outer stent diameter, and the wall thickness of the gasket was selected according to the desired wall thickness of the stent. The monomer mixture was introduced into the space between the coaxial tubes using a syringe and the mold was then exposed to an ultraviolet light source. After polymerization, the outer tube is cut away from the mold, the gaskets are removed and the polymer stent is removed from the inner tube.

Example 2

Characterization of Stress-Strain Properties

Copolymers having the compositions described in Tables 1–6 were prepared by introducing the mixture of components into a transparent mold. After polymerization, the stress-strain behavior of the polymers was characterized to determine the secant modulus at 100% strain and the strain at break using an Instron 5543. The dogbone-shaped test sample of each polymer was placed in the Instron at 37° C. and 100% humidity, to simulate in vivo conditions. At a speed of 1.5 in/min, the stress was increased. A plot of stress versus strain was generated for each sample. The secant modulus was obtained from the slope of a line drawn between the point on the stress-strain curve at 100% strain at the origin. The strain at break was taken as the point on the strain axis where the sample broke. The secant modulus at 100% strain and the strain at break are reported in Tables 1–6 above, for each of the exemplary polymers.

Although the invention has been described with respect to particular embodiments, it will be apparent to those skilled in the art that various changes and modifications can be made without departing from the invention.

It is claimed:

1. A stent for insertion into a lumen, comprising;
   a radially expandable, support stent having a selected axial length and an outer surface, said stent having rigid regions and flexible regions along its length; and
   one or more polymer members coaxially disposed about the outer surface of the support stent, said polymer members positioned over the rigid regions of the support stent, with the flexible regions exposed, and said polymer members being radially expandable with the support stent.

2. The stent of claim 1, wherein said polymer members are composed of (i) between 10–98% of a first monomer composed of an aliphatic ester C1–C50 of acrylic acid which when homopolymerized has a glass transition temperature lower than about 25° C.; and (ii) a second monomer having sites of unsaturation and capable of free radical polymerization, the second monomer when homopolymerized having a glass transition temperature greater than 25° C., said monomers when polymerized in the presence of a crosslinker forming a polymer having a glass transition temperature of less than about 25° C.

3. The stent of claim 2, wherein the first monomer is an aliphatic ester of methacrylic acid or an aliphatic ester of acrylic acid.

4. The stent of claim 2, wherein the first monomer is fluorinated.

5. The stent of claim 2, wherein the first monomer is selected from butyl acrylate and pentafluoropropylacrylate.

6. The stent of claim 2, wherein said second monomer is selected from the group consisting of an ester of methacrylic acid, polyethylene glycol methacrylate monomer and polyethyleneglycol monomethylether methacrylate monomer.

7. The stent of claim 2, wherein the second monomer is selected from the group consisting of methylmethacrylate, isobornyl methacrylate, isobutyl methacrylate, perfluoroacetylmethacrylate, tertiary butylmethacrylate, phenylethylmethacrylate, styrene, hydroxyethyl methacrylate, glycerol methacrylate, n-vinyl pyrrolidone and heptadecylfluorodecyl-methacrylate.

8. The stent of claim 2, wherein the first monomer is pentafluoropropylacrylate and the second monomer is heptadecylfluorodecyl methacrylate.

9. The stent of claim 2, which further includes a third monomer of a methacrylic acid ester of polyethyeneoxide, where the ester side chain has a molecular weight of between 200–10,000 Daltons.

10. The stent of claim 7, therein the third monomer is selected from the group consisting of polyethyleneglycol dimethacrylate, polyethyleneglycol methacrylate and polyethyleneglycol acrylate.

11. The stent of claim 9, wherein the first monomer is butyl acrylate, the second monomer is methylmethacrylate and the third monomer is polyethylene oxide.

12. The stent of claim 9, wherein the first monomer is pentafluoropropylacrylate and the second monomer is methylmethacrylate and the third monomer is polyethylene oxide.

13. The stent of claim 2, which further includes a therapeutic agent.

14. The stent of claim 2, wherein the polymer members are composed of (a) greater than about 40 weight percent of butyl acrylate monomer; (b) between 3–30 weight percent of methylmethacrylate monomer; (c) between 2–40 weight percent of polyethylene glycol monomethylether monomethyacrylate; said monomers when polymerized forming a polymer having a glass transition temperature of less than 25° C.

15. The stent of claim 14, wherein the polymer forming the polymer members further includes one or more of the following components:
   (a) between 0.1–20 weight percent of an organic solvent;
   (b) a monomer effective to impart a charge to the polymer at physiologic pH;
   (c) between 0.025–0.1 weight percent of a crosslinker;
   (d) between 0.1–1 weight percent of a photoinitiator;
   (e) a therapeutic agent.

16. The stent of claim 15, wherein the solvent is dimethylformamide in an amount between 1–15 weight percent.

17. The stent of claim 16, further including a therapeutic agent.

* * * * *